United States Patent
Beck et al.

(10) Patent No.: US 7,611,872 B2
(45) Date of Patent: Nov. 3, 2009

(54) METHOD FOR THE PRODUCTION OF D-PANTOTHENIC ACID AND/OR SALTS THEREOF VIA PURIFICATION BY NANOFILTRATION AS ADJUNCT FOR ANIMAL FEEDSTUFFS

(75) Inventors: Christine Beck, Mannheim (DE); Hans-Peter Harz, Dudenhofen (DE); Daniela Klein, Mannheim (DE); Martin Leemann, Bensheim (DE); Markus Lohscheidt, Mannheim (DE); Stefan Bitterlich, Dirmstein (DE); Hartwig Voβ, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 17 days.

(21) Appl. No.: 10/468,564

(22) PCT Filed: Feb. 20, 2002

(86) PCT No.: PCT/EP02/01754

§ 371 (c)(1),
(2), (4) Date: Aug. 21, 2003

(87) PCT Pub. No.: WO02/066664

PCT Pub. Date: Aug. 29, 2002

(65) Prior Publication Data

US 2004/0053374 A1   Mar. 18, 2004

(51) Int. Cl.
*C12P 13/04*   (2006.01)
(52) U.S. Cl. .................. 435/106; 210/650; 210/651; 210/652; 435/69.1
(58) Field of Classification Search ............. 435/106, 435/116, 69.1, 244; 210/650–652
See application file for complete search history.

(56) References Cited

U.S. PATENT DOCUMENTS 5,518,906 A * 5/1996 Hikichi et al. ............... 435/116
5,814,498 A * 9/1998 Mani et al. .................. 435/136
5,879,733 A * 3/1999 Ekanayake et al. .......... 426/271
5,932,457 A   8/1999 Moriya et al. ............... 435/146
5,952,206 A   9/1999 Giselbrecht et al.
6,126,754 A  10/2000 Duflot ......................... 127/55
6,171,845 B1  1/2001 Elischweski et al. ... 435/252.33
6,350,481 B1 * 2/2002 Kawachi et al. .............. 426/72
6,497,821 B1 * 12/2002 Bellamy et al. .............. 210/651
2004/0072307 A1 * 4/2004 Beck et al. ................... 435/106
2007/0202571 A1  8/2007 Eikmanns et al.

FOREIGN PATENT DOCUMENTS

| EP | 0 493 060 | 7/1992 |
| EP | 590 957 | 4/1994 |
| EP | 1 001 027 | 5/2000 |
| EP | 1 006 192 | 6/2000 |
| EP | 1 041 156 | 10/2000 |
| GB | 526267 | 6/1944 |
| WO | WO 97/10340 | 3/1997 |
| WO | WO 99/27124 | 6/1999 |
| WO | 01/21772 | 3/2001 |
| WO | WO-0205747 | 1/2002 |
| WO | 02/24001 | 3/2002 |
| WO | WO-02061108 | 8/2002 |

OTHER PUBLICATIONS

Bargeman et al., "Selective isolation of cationic amino acids and peptides by electro-membrane filtration," Lait 80:175-185, 2000.*
VWR International, Conversion of psi to bar and bar to psi, http://www.chromatography.co.uk/ Techniqs/Other/Pressure.htm, printed from the Internet on Jan. 11, 2005.*
XP-001002216, Baigori, Isolation and Characterization of *Bacillus subtilis* . . . 4240-4242.
XP-002171539.
XP-008004305, Begley, The Biosynthesis of Coenzyme A in Bacteria, 157-171.

* cited by examiner

*Primary Examiner*—Andrew Wang
*Assistant Examiner*—Rosanne Kosson
(74) *Attorney, Agent, or Firm*—Novak Druce + Quigg LLP (57) ABSTRACT

The invention relates to an improved method for the production of D-pantothenic acid and/or salts thereof and use thereof as adjunct for animal feedstuffs.

16 Claims, 7 Drawing Sheets

Table 1:

| Separation layer | Substructure (coarser than separation layer) |
|---|---|
| Metal | Metal |
| Ceramic | Metal, glass, ceramic or carbon |
| Polymer | Polymer, metal, ceramic or ceramic on metal |
| Carbon | Carbon, metal or ceramic |
| Ceramic: e.g. $\alpha\text{-}Al_2O_3$, $\gamma\text{-}Al_2O_3$, $ZrO_2$, $TiO_2$, SiC, mixed ceramic materials | |
| Polymer: e.g. PTFE, PVDF, polysulfone, polyether sulfone, polyether ether ketone, polyamide, polypropylene, polyacrylonitrile | |

Table 2:

| Manufacturer | Membrane | Cut-off limit (kD) Pore diameter (nm) |
|---|---|---|
| Atech innovations GmbH | TiO$_2$ on α-Al$_2$O$_3$/1.2 | 20 kD |
| | ZrO$_2$ on α-Al$_2$O$_3$/1.2 | 50 nm |
| | α-Al$_2$O$_3$ on α-Al$_2$O$_3$/1.2 | 100, 200 nm |
| Rhodia/Orelis | ZrO$_2$ or TiO$_2$ on ceramic/1.2 | 15, 50, 150 kD |
| | ZrO$_2$ on carbon/1 | 15, 50, 150 kD |
| | ZrO$_2$ or TiO$_2$ on ceramic/1.2 | 100, 200 nm |
| Graver Technologies | TiO$_2$ on steel/1 | 100 nm |
| Microdyn Modulbau GmbH | Homogeneous PP membrane/1 | 200 nm |
| NADIR Filtrations GmbH | Polyether sulfone/3 | 5-150 kD |
| | Cellulose/3 | 5-100 kD |
| | Polyacrylonitrile/1 | 20, 40 kD |
| | Polyether sulfone/1 | 40, 100 kD |
| Berghof | Polyarylether ketone on PP/1 | 5 kD |
| | Polysulfone on PP/1 | 5 to 20 kD |
| | Polyamide on PP/1 | 20 kD |
| Stork Friesland B.V. | PVDF/1 | 100 nm |
| | PVDF/1 | 30 nm |
| Osmonics/Desal | Modified polyacrylonitrile/3 | 100 kD |
| | Polysulfone/3 | 40 nm |
| Creavis | ZrO$_2$ on α-Al$_2$O$_3$ and metal/3 | 25, 80 nm |
| 1: tubular membrane; 2: multi-channel element; 3: flat membrane for coiled, bag, plate-stack or special modules having moving membrane or agitator aggregates between the membranes |||

Table 3:

Concentrating aqueous solution of Ca pantothenate 0.1 mol/kg and NaCl 0.2 mol/kg Apparatus   : 120 bar agitator pressure cell
Conditions  : 30°C/60 bar
Membrane    : Desal 5 DK

| Experiment | Date | Analysis via | Note | Retentate feed (g) | Retentate output (g) | Permeate output (g) | Analytical results | | | Permeate flux (kg/m²h) | | | Concentration factor MK | Yield | | Rejection rate (%) | |
|---|---|---|---|---|---|---|---|---|---|---|---|---|---|---|---|---|---|
| | | | | | | | Retentate feed | Retentate output | Permeate output | Start | Middle | End | | 1) | 2) | 1) | 2) |
| MgSO₄ | Feb. 28, 2001 | Con | | 1059 | 503 | 543 | 2.43 | 3.99 | 0.182 | | 137 | | 2.11 | | 0.96 | | 94.6 |
| 0108V01 | Jan. 3, 2001 | Chloride | | 1519.0 | 351.0 | 1172.6 | 0.201 | 0.145 | 0.212 | 61.9 | 28.1 | 9.6 | 4.33 | 0.17 | 0.18 | -22.1 | -14.4 |
| | | Chlorine ion | | 1519.0 | 351.0 | 1172.6 | 0.72 | 0.52 | 0.77 | | | | 4.33 | 0.17 | 0.17 | -22.2 | -16.1 |
| | | Ca | | 1519.0 | 351.0 | 1172.6 | 0.41 | 1.4 | 0.093 | | | | 4.33 | 0.79 | 0.82 | 83.8 | 87.0 |
| | | Na | | 1519.0 | 351.0 | 1172.6 | 0.45 | 0.63 | 0.38 | | | | 4.33 | 0.32 | 0.35 | 23.0 | 28.6 |
| | | Pantothenate | | 1519.0 | 351.0 | 1172.6 | 44.1 | 188 | 0 | | | | 4.33 | 0.99 | 1.00 | 99.0 | 100.0 |
| MgSO₄ | Feb. 3, 2001 | Con | | 897 | 495 | 409 | 2.43 | 4.51 | 0.456 | | 96 | | 1.81 | | 0.91 | | 85.3 |

Notes:
Membrane was installed new

Analysis:   Conductivity (con) → ZAT/C [mS/cm]
            Chloride → potentiometric titration at ZAT/C [mol/kg]
            Ca/Na/chlorine ion → ZAZ-M320 -
            microelement analysis [g/100 g]

1) calculated via balance in retentate
2) calculated via balance in permeate

Table 4:

Concentrating: aqueous solution of Na pantothenate 0.2 mol/l

Apparatus  : 120 bar agitator pressure cell
Conditions : 30°C/60 bar
Membrane   : Desal 5 DK

| Experi-ment | Date | Note | Analysis via | Reten-tate feed (g) | Reten-tate output (g) | Permeate output (g) | Analytical results | | | Permeate flux (kg/m²h) | | | Concen-tration factor MK | Yield | | Rejection rate (%) | |
|---|---|---|---|---|---|---|---|---|---|---|---|---|---|---|---|---|---|
| | | | | | | | Reten-tate feed | Reten-tate output | Per-meate output | Start | Mid-dle | End | | 1) | 2) | 1) | 2) |
| MgSO₄ | Apr. 9, 2001 | | Con | 807.0 | 412.2 | 404.2 | 2.33 | 4.07 | 0.126 | | 89.6 | | 1.96 | 0.89 | 0.97 | 83.0 | 96.1 |
| 0108V02 | Apr. 9, 2001 | | Chloride Chlorine ion | 989.40 989.40 | 230.50 230.50 | 754.40 754.40 | - - | - - | - - | 56.6 | 28.7 | 10.8 | 4.29 4.29 | | | | |
| | | | Ca Na Panto-thenate | 989.40 989.40 989.40 | 230.50 230.50 230.50 | 754.40 754.40 754.40 | 0.48 48.7 | 1.60 158.0 | 0.13 13.3 | | | | 4.29 4.29 4.29 | 0.77 0.76 | 0.80 0.76 | 82.1 80.8 | 84.1 83.8 |
| MgSO₄ | Apr. 9, 2001 | | Con | 805.9 | 387.0 | 413.6 | 2.33 | 4.16 | 0.321 | | 82.5 | | 2.08 | 0.86 | 0.93 | 79.0 | 89.8 |

Notes:

Analysis: Conductivity (con) → ZAT/C [mS/cm]
Chloride → potentiometric titration at ZAT/C [mol/kg]
Ca/Na/chlorine ion → ZAZ-M320 - microelement analysis [g/100 g]

1) calculated via balance in retentate
2) calculated via balance in permeate

Membrane used since February 28, 2001

Table 5

Concentrating: NaCl/CaCl₂ solution, equimolar

Apparatus   : 3.8 cm² test cell No. 34
Conditions  : 30°C/50 bar
Membrane    : Desal 5 DK

| Experiment | Date | Note | Analysis via | Retentate feed (g) | Retentate output (g) | Permeate output (g) | Analytical results | | | Permeate flux (kg/m²h) | | | Concentration factor MK | Yield | | Rejection rate (%) | |
|---|---|---|---|---|---|---|---|---|---|---|---|---|---|---|---|---|---|
| | | | | | | | Retentate feed | Retentate output | Permeate output | Start | Middle | End | | 1) | 2) | 1) | 2) |
| H₂O test | Sep. 28, 2001 | | | Water run at 30°C/30 bar | | | | | | | 394 | | | | | | |
| 0108VT01 | Oct. 1, 2001 | | Cl⁻<br>Ca²⁺<br>Na⁺ | 34.28<br>34.28<br>34.28 | 11.17<br>11.17<br>11.17 | 23.20<br>23.20<br>23.20 | 0.395<br>4.0<br>4.7 | 0.548<br>6.3<br>5.6 | 0.305<br>2.8<br>4.1 | 280 | 242 | 199 | 3.07<br>3.07<br>3.07 | 0.45<br>0.52<br>0.39 | 0.48<br>0.53<br>0.41 | 29.3<br>41.1<br>16.0 | 34.3<br>44.1<br>21.1 |
| 0108VT02 | Oct. 1, 2001 | | Cl⁻<br>Ca²⁺<br>Na⁺ | 34.22<br>34.22<br>34.22 | 11.28<br>11.28<br>11.28 | 23.13<br>23.13<br>23.13 | 0.395<br>4.0<br>4.7 | 0.533<br>6.4<br>5.8 | 0.305<br>2.8<br>4.1 | 286 | 249 | 210 | 3.03<br>3.03<br>3.03 | 0.45<br>0.53<br>0.41 | 0.48<br>0.53<br>0.41 | 27.1<br>42.2<br>19.5 | 34.4<br>44.2<br>21.4 |
| H₂O test | Oct. 1, 2001 | | | Water run at 30°C/30 bar | | | | | | | 335 | | | | | | |

Notes:
Membrane used since September 28, 2001

1) calculated via balance in retentate
2) calculated via balance in permeate

Analysis  Cl⁻ in equiv/kg → potentiometric titration at GCT/C
Ca²⁺, Na⁺ in % → ZAZ-M320 - Microelement analysis

METHOD FOR THE PRODUCTION OF D-PANTOTHENIC ACID AND/OR SALTS THEREOF VIA PURIFICATION BY NANOFILTRATION AS ADJUNCT FOR ANIMAL FEEDSTUFFS

This application is the U.S. national phase of International Application No. PCT/EP02/01754, filed on Feb. 20, 2002, which claims priority to German Application No. 10108226.6, filed on Feb. 21, 2001.

NAMES OF PARTIES TO A JOINT RESEARCH AGREEMENT

Subject matter described and claimed in the instant patent was developed pursuant to a joint research agreement between OmniGene Bioproducts, Inc. and BASF Aktiengesellschaft.

The present invention relates to an improved process for preparing D-pantothenic acid and/or salts thereof and the use as additive to animal feedstuffs.

TECHNICAL FIELD

D-pantothenate is widespread in the plant and animal kingdom as a starting product for the biosynthesis of coenzyme A. In contrast to humans, who consume pantothenic acid in sufficient quantities via the diet, symptoms of D-pantothenate deficiency are, however, frequently described not only for plants but also for animals. The availability of D-pantothenate is therefore of great economic interest, in particular in the animal feed industry.

Conventionally, D-pantothenate is prepared by chemical synthesis from D-pantolactone and calcium β-alaninate (Ullmann's Encyclopedia of Industrial Chemical, 6th edition, 1999, electronic release, Chapter "Vitamins"). To prepare D-pantolactone, a complex classical racemate separation via diastereomeric salts is required. The commercial product resulting from the chemical synthesis is usually the calcium salt of D-pantothenic acid, calcium D-pantothenate.

Compared with chemical synthesis, the advantage of biotechnological preparation processes using microorganisms is in the selective (enantiomerically pure) provision of the D form of pantothenic acid which can be utilized by higher organisms. A complex racemate separation as is required in chemical synthesis is thus unnecessary.

BACKGROUND ART

Fermentation processes for preparing D-pantothenic acid by microorganisms have been disclosed in great number, including by EP 0 590 857, WO 96/33283; U.S. Pat. No. 6,013,492, WO 97/10340, DE 198 46 499, EP 1 001 027, EP 1 006 189, EP 1 006 192 and EP 1 006 193.

Thus EP 1 006 189 and EP 1 001 027 describe processes for preparing pantothenate in which the fermentation solution reaches a content of at most 1 g/l of D-pantothenic acid. However, such low pantothenic acid contents in the fermentation solution, that is to say less than 10% by weight based on the solids content, are unsuitable for economic production of D-pantothenic acid-containing animal feed supplements. A further disadvantage of the processes described to date is that isolating the product from the fermentation medium requires numerous complex work-up steps. An economic production process for the industrial scale has not been disclosed.

In the German laid-open application DE 100 16 321, a fermentation process is described for producing a D-pantothenic-acid-containing animal feed supplement. However, a significant disadvantage of this process, as also with the fermentation processes cited above for D-pantothenic acid production, is that the pantothenic acid precursor β-alanine has to be supplied to the microorganism via the fermentation medium in order to obtain economic yields of the desired product.

In addition U.S. Pat. No. 6,013,492 and WO 96/332839 describe the work-up of D-pantothenic acid from the fermentation solution by filtering off insoluble constituents (e.g. cell material) from the culture medium, adsorbing the filtrate to activated carbon, subsequently eluting the D-pantothenic acid with an organic solvent, preferably methanol, neutralizing the eluent with calcium hydroxide, and finally crystallizing calcium D-pantothenate. Significant disadvantages are the losses of product of value which occur during the crystallization and the use of an organic solvent which may be removed from the product only with difficulty and requires complex solvent recovery.

EP 0 590 857 describes a fermentation process for producing D-pantothenic acid in which culturing a microorganism obligatorily requires supply of β-alanine. The fermentation solution is filtered to separate off the biomass, then passed through a cationic exchanger and then through an anionic exchanger, is then neutralized with calcium hydroxide, concentrated by evaporation, admixed with activated carbon, filtered once more and crystallized with addition of methanol and calcium chloride. The resultant calcium-pantothenate-containing product, in addition to D-pantothenic acid in the form of the calcium salt, also contains calcium chloride in a molar ratio of 1:1. To reduce the calcium chloride content, electrodialysis with subsequent spray-drying is necessary. This process has the disadvantage, because of the multiplicity of complex process steps and the use of organic solvents, of being neither economic nor ecological.

DISCLOSURE OF INVENTION

It is an object of the present invention to provide an animal feed supplement containing D-pantothenic acid and/or salts thereof and also the production thereof by an improved process for preparing D-pantothenic acid and/or salts thereof which does not have the disadvantages mentioned above. In this case, for economic reasons, a process is desirable in which supply of β-alanine is drastically reduced or is not required at all. In addition, it is desirable to prepare D-pantothenic acid in the form of its divalent salts and, in this case especially the alkaline earth metal salts, since the divalent salts have lower hygroscopic properties than monovalent salts of pantothenic acid and for further use, for example as animal feed supplement, thus have a less pronounced tendency toward aggregation.

We have found that this object is achieved in an advantageous manner by the present invention.

The present invention relates to a process for preparing D-pantothenic acid and/or salts thereof, which comprises a) using at least one D-pantothenic-acid-producing organism, the pantothenic acid (pan) and/or isoleucine/valine (ilv) biosynthesis of which is deregulated and which forms at least 2 g/l of salts of D-pantothenic acid by fermentation in a culture medium, with 0-20 g/l of free β-alanine and/or β-alanine salt being fed to the culture medium, b) salts containing polyvalent cations being fed to the D-pantothenate formed, polyvalent salts of D-pantothenic acid being formed, c) the solution containing polyvalent salts of D-pantothenic acid being worked up by nanofiltration, the polyvalent salts of D-pantothenic acid being enriched and
d) the nanofiltration retentate containing polyvalent salts of D-pantothenic acid being subjected to drying and/or formulation.

MODE(S) FOR CARRYING OUT THE INVENTION

In a variant of the inventive process, the retentate from step c) is a suspension containing polyvalent salts of D-pantothenic acid.

In addition, the fermentation can be carried out by procedures known per se in the batch, fed-batch or repeated fed-batch mode or under continuous process procedures. For neutralizing the resulting pantothenic acid, customary buffer systems are used in this case, for example phosphate buffer containing NaOH, KOH or ammonia.

In further variants of the inventive process, in step a), at least 10 g/l, preferably at least 20 g/l, particularly preferably at least 40 g/l, very particularly preferably at least 60 g/l, and in particular at least 70 g/l of salts of D-pantothenic acid are formed in the culture medium by fermentation.

DETAILED DESCRIPTION OF THE INVENTION

For the purposes of the present invention, the formulation "produce" means that the organism can synthesize greater amounts of D-pantothenic acid and/or salts thereof than are required for its own metabolic needs. In an inventively advantageous variant, the amount of D-pantothenic acid and/or salts thereof which is synthesized is not present in the cell interior, but, ideally, is completely released into the culture medium from the organism. This secretion can take place actively or passively by mechanisms which are known per se.

According to the invention, the D-pantothenic-acid-producing organisms used are microorganisms. These include, according to the invention, fungi, yeasts and/or bacteria. According to the invention preference is given to fungi, for example Mucor, or yeasts, for example *Saccharomyces* or *Debaromyces* [sic] and, in this case, preference is given to using *Saccharaomyces* [sic] *cerevisiae*. Advantageously according to the invention *coryneform* bacteria or Bacillaceae are used. Those which are covered according to the invention are preferably, for example, bacteria of the genera *Corynebacterium, Escherichia, Bacillus, Arthrobacter, Bevibacterium, Pseudomonas, Salmonella, Klebsiella, Proteus, Acinetobacter* or *Rhizobium*. Particular preference is given here, for example, to *Corynebacterium glutamicum, Brevibacterium breve* or *Baccillus subtilis, B. licheniformis, B. amyloliquefaciens, B. cereus, B. lentimorbus, B. lentus, B. firmus, B. pantothenticus, B. circulans, B. coagulans, B. megaterium, B. pumilus, B. thuringiensis, B. brevis, B. stearothermophilus* and other *bacillus* species of group 1 which are characterized by their 16sRNA, or *Actinum mycetalis*. This listing serves for illustration and is in no way limiting for the present invention.

Furthermore, the present invention also comprises the use of genetically modified organisms for the inventive preparation of an animal feed supplement containing free D-pantothenic acid and/or salts thereof. Such genetically modified organism can be isolated, for example, by chemical mutagenesis and subsequent selection by a suitable "screening method". The invention also comprises what are termed "production strains", which are suitable for producing the product within the meaning of the present invention and have genetic modifications with respect to metabolic flux in the direction of the D-pantothenic acid, other modifications with respect to the secretion of D-pantothenic acid and/or salts thereof through the cell membrane also being included. This can be achieved, for example, by modifications at key positions in relevant metabolic biosynthesis pathways of the organism used.

It is also conceivable to use transgenic organisms which result from the transfer of homologous and/or heterologous nucleotide sequences which are required or can be beneficial for the synthesis of the desired product. In this case the overexpression and/or deregulation of one of more genes individually and/or in combination, localized in the genome and/or on a vector is conceivable.

Such transgenic organisms can contain, advantageously, additional copies of and/or genetically modified genes selected from the group consisting of panB, panC, panD, panE and/or combinations thereof and/or even organizational units, such as the panBCD operon. In addition, further metabolic pathways, for example the isoleucine-valine biosynthetic pathway can be advantageously manipulated in the organisms, for example as described in EP 1 006 189, EP 1 006 192, EP 1 006 193 or EP 1 001 027. By this means, branched-chain precursor substances of pantothenic acid biosynthesis are provided in greater quantity. Advantageously, if appropriate, the genes for this biosynthetic pathway, that is to say ilvB, ilvN, ilvC and/or ilvD, are overexpressed.

Furthermore, genetic modifications of aspartate-$\alpha$-decarboxylase (panD), for example by overexpression and/or deregulation, are comprised according to the invention in the D-pantothenic-acid-producing organism used.

For the purposes of the present invention, the formulation "deregulation" means the following: change or modification of at least one gene which codes for an enzyme in a biosynthetic metabolic pathway, so that the activity of the enzyme in the microorganism is changed or modified. Preferably, at least one gene which codes for an enzyme of a biosynthetic metabolic pathway is altered in such a manner that the gene product is formed to an increased extent or has an increased activity. The term "deregulated metabolic pathway" also includes a biosynthetic metabolic pathway in which more than one gene which codes for more than one enzyme is changed or modified in such a manner that the activities of more than one enzyme are changed or modified.

Changes or modifications can comprise, but are not limited to: removing the endogenous promoter or regulatory elements; introducing strong promoters, inducible promoters or a plurality of promoters simultaneously; removing regulatory sequences, so that the expression of the gene product is changed; changing the chromosomal position of the gene; changing the DNA sequence in the vicinity of the gene or within the gene, for example of the ribosomal binding site (RBS); increasing the number of copies of the gene in the genome or by introducing plasmids of differing number of copies; modification of proteins (e.g. regulatory proteins, suppressors, enhancers, transcriptional activators and the like) which play a role in the transcription of the gene and/or in the translation to give the gene product. These also include all other possibilities for deregulating the expression of genes which are prior art, for example the use of antisense oligonucleotides, or the blocking of repressor proteins.

Deregulation can also comprise changes in the coding region of genes which lead, for example, to removing feedback regulation in the gene product or to a higher or lower specific activity of the gene product.

Furthermore, according to the invention genetic engineering changes to enzymes are advantageous which effect the efflux of precursors of pantothenic acid and/or the flux of pantothenic acid to coenzyme A. Examples of such enzyme-coding genes are: alsD, avtA, ilvE, ansB, coaA, coaX etc. This listing serves for illustration and is in no way limiting for the present invention.

In addition, genetic engineering changes are advantageous which secure the cellular provision of cofactors (for example of methylene tetrahydrofolate, redox equivalents etc.) in an amount optimum for pantothenic acid production.

Advantageously, β-alanine is thus already present in the cells at increased concentrations compared with correspondingly non-genetically modified organisms, and thus need not be added as a precursor to the culture medium, as is required, for example, in EP-A-0 590 857. Microorganisms are advantageous in which pantothenic acid (pan) and/or isoleucine/valine (ilv) biosynthesis and/or asparate [sic] α-decarboxylase (panD) is deregulated. Furthermore, an additional overexpression of ketopanthoate reductase (panE) in the microorganisms is advantageous.

It is further advantageous according to the invention if the coaA gene, which is required for the synthesis of coenzyme A, if appropriate is reduced in activity or (for example in Bacillus species) is entirely switched off. This is because Bacillus, in addition to coaA, contains a further gene for this enzymatic function (=coaX). The activity of this coaX gene or of the corresponding enzyme can also be altered, preferably reduced, or even deleted, provided that coaA itself still has sufficient, even if decreased, enzyme activity, that is to say the enzyme activity of coaA has not entirely been lost. In addition to overexpressing the various genes, genetic manipulation of the promoter regions of these genes is advantageous in such a manner that this manipulation leads to an overexpression of the gene products.

In a variant embodiment of the present invention, the bacterial strains described according to the annex (PCT/US application 0025993), for example Bacillus subtilis PA824 and/or derivatives thereof are used. In a further variant embodiment, according to the invention the microorganism Bacillus subtilis PA668, as described according to the annex (U.S. serial No. 60/262,995) is used in the inventive process. These strains Bacillus subtilis PA824 and PA668 were produced as follows:

Starting from the strain Bacillus subtilis 168 (Marburg strain ATCC 6051), which has the genotype trpC2 (Trp⁻), the strain PY79 was produced via transduction of the Trp⁺ marker (from the Bacillus subtilis wild type W23). ΔpanB and ΔpanE1 mutations were introduced into strain PY79 by classical genetic engineering methods (as described, for example, in Harwood, C. R. and Cutting, S. M. (editors), Molecular Biological Methods for Bacillus (1990) John Wiley & Sons, Ltd.; Chichester, England).

The resultant strain was transformed using genomic DNA of Bacillus subtilis strain PA221 (genotype $P_{26}$panBCD, trpC2 (Trp⁻)) and genomic DNA from Bacillus subtilis strain PA303 (genotype $P_{26}$panE1). The resultant strain PA327 has the genotype $P_{26}$panBCD, $P_{26}$panE1 and is a typotophan auxotroph (Trp⁻). Using the Bacillus subtilis strain PA327, in 10 ml cultures using SVY medium (25 g/l of Difco Veal Infusion Broth, 5 g/l of Difco Yeast Extract, 5 g/l of Na glutamate, 2.7 g/l of ammonium sulfate, make up to 740 ml with water, autoclave, then add 200 ml of 1 M potassium phosphate, pH 7.0 and 60 ml of 50% sterile glucose solution), which had been supplemented with 5 g/l of β-alanine and 5 g/l of α-ketoisovalerate, pantothenic acid titers of up to 3.0 g/l (24 h) was [sic] achieved.

The preparation of Bacillus subtilis strain PA221 (genotype $P_{26}$panBCD, trpC2 (Trp⁻)) is described in the following section:

By classical genetic engineering methods, with the aid of the sequence information of the panBCD operon of E. coli (see Merkel et al., FEMS Microbiol. Lett., 143 1996:247-252), starting from a Bacillus subtilis GP275 plasmid library, the panBCD operon of Bacillus was cloned. For the cloning, the E. coli strain BM4062 (bir$^{rs}$) was used, as was the information that the Bacillus operon is in the vicinity of birA gene. The panBCD operon was introduced into a plasmid which can replicate in E. coli. To improve the expression of the panBCD operon, strong constitutive promoters of Bacillus subtilis phages SP01 ($P_{26}$) were used and the ribosome binding site (=RBS) in front of the panB gene was replaced by an artificial RBS. A DNA fragment which is immediately upstream of the native panB gene in Bacillus, was ligated in front of the $P_{26}$panBCD cassette on the plasmid. This plasmid was transformed into the Bacillus subtilis strain RL-1 (derivative of Bacillus subtilis 168 obtained by classical mutagenesis (Marburg strain ATCC 6051), genotype trpC2 (Trp⁻)) and, by homologous recombination, the native panBCD operon was replaced by the $p_{26}$panBCD operon. The resultant strain is termed PA221 and has the genotype $P_{26}$panBCD, trpC2 (Trp⁻).

Using the Bacillus subtilis strain PA221, in 10 ml cultures with SVY medium which have been supplemented with 5 g/l of β-alanine and 5 g/l of α-ketoisovalerate, pantothenic acid titers of up to 0.92 g/l (24 h) was [sic] achieved.

Production of the Bacillus subtilis strain PA303 (genotype $P_{26}$panE1) is described in the following section:

With the aid of the E. coli pane gene sequence, the Bacillus panE sequence was similarly cloned. It was found that two homologs of the panE gene of E. coli exist in B. subtilis which are termed panE1 and panE2. By deletion analysis, it was found that the panE1 gene is responsible for 90% of pantothenic acid production, while deleting the panE2 gene had no significant effect on the pantothenic acid production. Here also, in a similar manner to cloning the panBCD operon, the promoter was replaced by the strong constitutive promoter $P_{26}$ and the ribosome binding site before the panE1 gene was replaced by the artificial binding site. The $P_{26}$panE1 fragment was cloned into a vector which was designed so that the $P_{26}$panE1 fragment could integrate into the original panE1 locus in the genome of Bacillus subtilis. The strain resulting after transformation and homologous recombination is termed PA303 and has the genotype $P_{26}$panE1.

Using the Bacillus subtilis strain PA303, in 10 ml cultures using SVY medium which had been supplemented with 5 g/l of β-alanine and 5 g/l of α-ketoisovalerate, pantothenic acid titers of up to 1.66 g/l (24 h) was [sic] achieved.

Further strain construction proceeded via transformation of PA327 using a plasmid which contains the $P_{26}$ilvBNC operon and the marker gene for spectinomycin. The $P_{26}$ilvBNC operon integrated into the amyE locus, which was demonstrated by PCR. One transformant was termed PA340 (genotype $P_{26}$panBCD, $P_{26}$panE1, $P_{26}$ilvBNC, specR, trpC2 (Trp⁻)).

Using the Bacillus subtilis strain PA340, in 10 ml cultures using SYV medium which had only been supplemented with 5 g/l of β-alanine, pantothenic acid titers of up to 3.6 g/l (24 h) was [sic] achieved, and in 10 ml cultures using SVY medium which had been supplemented with 5 g/l of β-alanine and 5 g/l of α-ketoisovalerate, pantothenic acid titers of up 4.1 g/l (24 h) were achieved.

In addition, a deregulated ilvD cassette was introduced into strain PA340. For this, a plasmid containing the ilvD gene under the control of the $P_{26}$ promoter having the artificial RBS2 was transformed into PA340. In this case the $P_{26}$ilvD gene was integrated into the original ilvD locus by homologous recombination. The resultant strain PA374 has the genotype $P_{26}$panBCD, $P_{26}$panE1, $P_{26}$ilvBNC, $P_{26}$ilvD, specR and trpC2 (Trp$^-$).

Using the *Bacillus subtilis* strain PA374, in 10 ml cultures using SVY medium which was supplemented only with 5 g/l of β-alanine, pantothenic acid titers of up to 2.99 g/l (24 h) was [sic] achieved.

To produce pantothenic acid using strain PA374 without supplying β-alanine, additional copies of the gene panD coding for aspartate α-decarboxylase were introduced into strain PA374. For this, chromosomal DNA of strain PA401 was transformed into PA374. The strain PA377 was obtained by selection on tetracycline.

The resultant strain PA377 has the genotype $P_{26}$panBCD, $P_{26}$panE1, $P_{26}$ilvBNC, $P_{26}$ilvD, specR, tetR and trpC2 (Trp$^-$).

Using the *Bacillus subtilis* strain PA377, in 10 ml cultures using SVY medium, precursor-supply-free pantothenic acid titers of up to 1.3 g/l (24 h) was [sic] achieved.

The preparation of the *Bacillus subtilis* strain PA401 (genotype $P_{26}$panD) is described in the following section:

The *Bacillus subtilis* panD gene was cloned from the panBCD operon into a vector bearing the tetracyclin marker gene. The promoter $P_{26}$ and an above-described artificial RBS were cloned in front of the panD gene. By restriction digestion, a fragment containing the tetracyclin marker gene and the $P_{26}$panD gene was produced. This fragment was religated and transformed into the above-described strain PA221. The fragment integrated into the genome of strain PA211. The resultant strain PA401 has the genotype $P_{26}$panBCD, $P_{26}$panD, tetR and trpC2 (Trp$^-$).

Using *Bacillus subtilis* strain PA401, in 10 ml cultures in SVY medium which had been supplemented with 5 g/l of α-ketoisovalerate, pantothenic acid titers of up to 0.3 g/l (24 h) was [sic] achieved. In 10 ml cultures using SVY medium which had been supplemented with 5 g/l of D-pantoin acid and 10 g/l of L-aspartate, pantothenic acid titers of up to 2.2 g/l (24 h) were achieved.

Starting from strain PA377, by transformation with chromosomal DNA from strain PY79, a tryptophan prototroph strain was generated. This strain PA824 has the genotype $P_{26}$panBCD, $P_{26}$panE1, $P_{26}$ilvBNC, $P_{26}$ilvD, specR, tetR and Trp$^+$.

Using *Bacillus subtilis* strain PA824, in 10 ml cultures in SVY medium, precursor-supply-free pantothenic acid titers of up to 4.9 g/l (48 h) was [sic] achieved (control PA377: up to 3.6 g/l in 48 h). The exact construction of the strains is as given according to the annex of PCT/US application 0025993.

The preparation of PA668 is described in the following section:

The *Bacillus* panB gene was cloned from the wild type panBCD operon and inserted into a vector which, in addition to a chloramphenicol resistance gene, also contains *B. subtilis* sequences of the vpr locus.

The strong constitutive promoter $P_{26}$ was introduced in front of the 5' end of the panB gene. A fragment which contains the $P_{26}$panB gene, the marker gene for chloramphenicol resistance and *Bacillus subtilis* vpr sequences was obtained by restriction digestion. The isolated fragment was religated and the strain PA824 was transformed therewith.

The resultant strain was termed PA668. The genotype of PA668 is: $P_{26}$panBCD, $P_{26}$panE1, $P_{26}$ilvBNC, $P_{26}$ilvD, $P_{26}$panB, specR, tetR, CmR and Trp$^+$.

Two colonies of PA668 were isolated and termed PA668-2A, and the other PA668-24.

Using *B. subtilis* strain PA668-2A, in 10 ml cultures in SVY medium without supply of precursors, pantothenic acid titers of 1.5 g/l are achieved in 48 h. In 10 ml cultures which are supplemented with 10 g/l of aspartate, titers up to 5 g/l are achieved. Using *B. subtilis* strain PA668-24, in 10 ml cultures in SVY medium without supplying precursors, pantothenic acid titers of 1.8 g/l are achieved in 48 h. In 10 ml cultures supplemented with 10 g/l of L-aspartate, titers up to 4.9 g/l are achieved.

The exact construction of the strains is given according to the annexes of PCT/US application 0025993 and U.S. serial No. 60/262,995.

Using the above-described strain PA377, in glucose-limited fermentation in SVY medium (25 g/l of Difco Veal Infusion Broth, 5 g/l of Difco Yeast Extract, 5 g/l of tryptophan, 5 g/l of Na glutamate, 2 g/l of $(NH_4)_2SO_4$, 10 g/l of $KH_2PO_4$, 20 g/l of $K_2HPO_4$, 0.1 g/l of $CaCl_2$, 1 g/l of $MgSO_4$, 1 g/l of sodium citrate, 0.01 g/l of $FeSO_4 \cdot 7H_2O$ and 1 ml/l of a trace salt solution of the following composition: 0.15 g of $Na_2MoO_4 \cdot 2H_2O$, 2.5 g of $H_3BO_3$, 0.7 g of $CoCl_2 \cdot 6H_2O$, 0.25 g of $CuSO_4 \cdot 5H_2O$, 1.6 g of $MnCl_2 \cdot 4H_2O$, 0.3 g of $ZnSO_4 \cdot 7H_2O$ made up to 1 l with water)) on a 10 l scale with continuous supply of a glucose solution, pantothenic acid concentrations of 18-19 g/l (22-25 g/l) in the fermentation broth are achieved in 36 h (48 h).

In glucose-limited fermentation of PA824, the tryptophan-prototroph derivative of PA377, in yeast extract medium (10 g/l of Difco Yeast Extract, 5 g/l of Na glutamate, 8 g/l of $(NH_4)_2SO_4$, 10 g/l of $KH_2PO_4$, 20 g/l of $K_2HPO_4$, 0.1 g/l of $CaCl_2$, 1 g/l of $MgSO_4$, 1 g/l of sodium citrate, 0.01 g/l of $FeSO_4 \cdot 7H_2O$ and 1 ml/l of the above-described trace salt solution) on a 10 l scale with continuous supply of a glucose solution, the following pantothenic acid concentrations are achieved in fermentation broths in 36 h, 48 h and 72 h: 20 g/l, 28 g/l and 36 g/l.

By further media optimization, using strain PA824 in glucose-limited fermentation in a medium consisting of 10 g/l of Difco Yeast Extract, 10 g/l of NZ amine A (Quest International GmbH, Erftstadt), 10 g/l of Na glutamate, 4 g/l of $(NH_4)_2SO_4$, 10 g/l of $KH_2PO_4$, 20 g/l of $K_2HPO_4$, 0.1 g/l of $CaCl_2$, 1 g/l of $MgSO_4$, 1 g/l of sodium citrate, 0.01 g/l of $FeSO_4 \cdot 7H_2O$ and 1 ml/l of the above-described trace salt solution on a 10 l scale with continuous supply of a glucose solution, pantothenic acid concentrations of 37 g/l (48 g/l) is [sic] achieved in fermentation broths in 36 h (48 h).

Further increases in pantothenic acid concentration in the fermentation broth are conceivable by further media optimization, by increasing the fermentation time, by process and strain improvement and by combinations of the individual steps. Thus the above-described pantothenic acid concentrations may also be achieved by fermentation of strains which are derivatives of the above-described PA824. Derivatives can be produced by classical strain development and by further genetic engineering manipulations. By development of media, strain and fermentation processes, the pantothenic acid titers in the fermentation broths can be increased to greater than 40, 45, 50, 55, 60, 65, 70, 75, 80, 85 and >90 g/l.

An important advantage of the inventive process is that the fermentation is carried out in a culture medium which, apart from at least one carbon and nitrogen source as starting compounds does not contain further precursors. That is to say the biosynthesis of D-pantothenic acid is independent of the supply of further precursors. For the purposes of the present invention such precursors are, for example, β-alanine and/or L-aspartate and/or L-valine and/or α-ketoisovalerate and/or combinations thereof.

In a preferred variant of the inventive process, the fermentation of the D-pantothenic-acid-producing organism is carried out in a culture medium which contains a carbon source and a nitrogen source, to which, however, no free β-alanine and/or β-alanine salts are added or is carried out in the course of the fermentation. That is to say, to produce D-pantothenic acid in ranges of at least 10 g/l of culture medium, preferably at least 20 g/l, particularly preferably at least 40 g/l, very particularly preferably at least 60 g/l, and in particular at least 70 g/l, according to the invention no supply of free β-alanine and/or β-alanine salts is necessary.

The independence of the supply of precursors is, in particular, an important economic advantage of the inventive process compared with known processes, since a multiplicity of precursors are very expensive.

However, adding β-alanine and/or β-alanine salts is not excluded according to the invention, so that therefore the yield of D-pantothenic acid can be further improved by adding β-alanine and/or β-alanine salts. Assuming, for example, that all required precursors of pantothenic acid are present in a sufficient amount, only the activity of the panD gene limits a further increase in pantothenic acid production, then the yield of pantothenic acid can be increased, for example, by a further 50% by adding free β-alanine and/or β-alanine salts.

In an advantageous variant of the present invention, up to 20 g/l of free β-alanine and/or β-alanine salts can be added to the culture medium for additional increase in pantothenic acid yield by more than 50%. Preference is given to adding about 15 g/l of free β-alanine and/or β-alanine salts to the culture medium.

Examples of carbon sources suitable according to the invention for use in a culture medium for fermentation of the abovementioned organisms are sugars, such as starch hydrolyzates (mono-, di-, oligosaccharides), preferably glucose or sucrose, and also beet or cane sugar molasses, proteins, protein hydrolyzates, soybean flour, corn steep liquor, fats, free fatty acids, recirculated cells from fermentations carried out previously or hydrolyzates thereof and also yeast extract. These listings are not limiting for the present invention.

In addition, the present invention is advantageously distinguished in that the total sugar content is reduced to a minimum toward the end of the fermentation, since otherwise this makes difficult the later drying and/or formulation of the fermentation solution due to sticking. This can be achieved according to the invention by carrying on the fermentation for some further time after the carbon source is exhausted (in the case of batch culture) or after the carbon feed (in the case of fed-batch or repeated fed-batch process conditions) is interrupted and/or regulated in such a manner that the concentration of the carbon source is virtually zero (in the case of fed-batch, repeated fed-batch or continuous process conditions).

This is carried out according to the invention by carrying on the fermentation, after interruption in addition of the carbon source (for example sugar solution), until the dissolved oxygen concentration ($pO_2$) reaches at least 80%, preferably 90% and particularly preferably 95%, of the saturation value in the fermentation solution.

Examples of nitrogen sources suitable according to the invention are ammonia, ammonium sulfate, urea, proteins, protein hydrolyzates or yeast extract. This listing is also not limiting for the present invention.

In addition, the fermentation medium contains mineral salts and/or trace elements, such as amino acids and vitamins. The exact compositions of suitable fermentation media are known in large numbers and accessible to those skilled in the art.

After inoculating the fermentation medium with a suitable D-pantothenic-acid-producing organism (at cell densities known to those skilled in the art), if appropriate with addition of an antifoam, the organism is cultured. Any necessary regulation of the medium pH can be carried out using various inorganic or organic alkali metal hydroxide solutions or acids, for example NaOH, KOH, ammonia, phosphoric acid, sulfuric acid, hydrochloric acid, formic acid, succinic acid, citric acid or the like.

Owing to the buffer systems used during the fermentation, which can be as previously described, for example NaOH, KOH, ammonia, phosphoric acid, sulfuric acid, hydrochloric acid, formic acid, succinic acid, citric acid or the like, the D-pantothenic acid formed in the fermentation solution, depending on the buffer system used, is present in the form of the respective salt(s). Since in this case, in particular, the salts of D-pantothenic acid in the form of their monovalent cations are disadvantageous, the fermentation solution is worked up according to the invention by nanofiltration.

For this, salts containing polyvalent cations are first fed according to the invention to the D-pantothenate formed, which forms polyvalent salts of D-pantothenic acid. According to the invention, salts containing polyvalent cations can be added in solid form or in aqueous solution during, preferably at the end of, or after, the fermentation in step a). An aqueous solution containing polyvalent cations can be fed, for example, continuously.

In addition, in a step upstream of the nanofiltration, that is to say before the nanofiltration in step c) of the inventive process, cell mass or components precipitated in the solution can be separated off. In this case the separation can be performed by decanting or membrane filtration, preferably ultrafiltration. In a variant of the inventive process, the membrane filtration is carried out as diafiltration. Here also, according to the invention salts containing polyvalent cations can be added in solid form or aqueous solution during, or after, a membrane filtration of a D-pantothenate-containing solution. For example, an aqueous solution containing polyvalent cations is fed here continuously.

In the separation of cell mass and/or components precipitated out in the solution, for example slightly soluble or insoluble phosphate salts or sulfate salts, enzymes, hormones, proteins, antibiotics, pyrogens, viruses, polysaccharides, colloids, surfactants, pesticides or other inorganic substances, the separation is based on the utilization of gravity, centrifugal force, pressure or vacuum. Exemplary processes are, inter alia: decanting, elutriation, sieving, wind-classification, classification, filtration, dialysis, sedimentation, microfiltration, ultrafiltration, flotation, foam fractionation, sink-swim separation, clarification, centrifugation or separation. Membrane separation processes, such as microfiltration or ultrafiltration, operated by a pressure difference between feed side and permeate side are summed up as membrane filtration. The processes differ, for example, by their separation limits. Thus, in the case of ultrafiltration, the cut-off limit is not based on the particle size, for example as in the case of microfiltration, but on the molar mass which is in the range from about $10^3$ to $2\times10^6$ Da. In ultrafiltration, in addition to the filtrate (permeate), what is known as the concentrate (retentate) is also produced.

To separate off solid substances, or enrich or deplete dissolved medium-molecular-weight and high-molecularweight substances, advantageously asymmetrically structured porous membranes are used.

The membranes used according to the invention can, in an advantageous variant, be made up of a separation layer, which effects the actual separation, and a one layer or multilayered supporting layer which bears the separation layer and has coarser pores than the separation layer. The separation layers and the supporting layer can consist of organic or inorganic polymers, ceramic, metal or carbon and must be stable in the reaction medium and at the process temperature. Examples of these are listed in table 1, but are not limiting for the present invention:

The membranes can be used in the form of flexible tubing, tubes, capillaries, hollow fibers or flat membranes in flat, tubular, multi-channel element, capillary or coiled modules which are known per se.

The optimum transmembrane pressures between retentate and permeate are essentially from 1 to 40 bar, depending on the diameter of the membrane pores or the cut-off limit (expressed in molecular weight units), the mechanical stability of the membrane and the type of membrane. Higher transmembrane pressures generally lead to higher permeate fluxes. In the case in which the feed (solution to be treated) is fed at an excessive pressure, the transmembrane pressure can be adapted by increasing the permeate pressure.

The operating temperature is dependent on the product stability and membrane stability. It is from about 20 to 90° C., preferably from about 40 to 70° C. Higher temperatures lead to higher permeate fluxes. Membranes according to table 2 can be used, for example, but these are not limiting for the present invention.

Cell separation, according to the invention, can advantageously also be performed by a special type of membrane filtration, that is to say diafiltration. Diafiltration can take place batchwise by passing the solution containing polyvalent salts of D-pantothenic acid via a circuit comprising a vessel, a pump and one or more membrane modules and setting the pressures in the membrane modules in such a manner that permeate is produced. Continuously, or at certain times, water or an aqueous solution is added which does not contain the product to be removed, or contains it at a lower concentration than at the timepoint of addition to the separation circuit. According to the invention, the aqueous solution can contain salts of polyvalent cations, for example calcium or magnesium halides or combinations thereof, preferably calcium chloride and/or magnesium chloride.

The cell removal by means of diafiltration can according to the invention also be performed continuously, with preferably a plurality of membrane modules being connected in series, or in each case one or more membrane-module-containing pump circuits being connected in series. Upstream of, between or downstream of the membrane modules or pump circuits, water or an aqueous solution which does not contain the product to be removed or only contains it at lower concentration than at the feed site can be added, in which case, as in the batch variant, the aqueous solution can contain salts of polyvalent cations, for example calcium or magnesium halides or combinations thereof, preferably calcium chloride and/or magnesium chloride.

According to the invention the ultrafiltration or diafiltration can be carried out directly using the fermentation output, or after a treatment of the fermentation output, for example by centrifugation, decanting or similar procedure.

If according to the invention cell mass or components precipitated out in the solution are removed, the addition of salts containing polyvalent cations according to step b) of the inventive process can take place during, or after, the ultrafiltration or diafiltration. In variants of the inventive process, polyvalent cations added are, for example, calcium and/or magnesium chloride, nitrate, hydroxide, formate, acetate, propionate, glycinate and/or lactate. In this case the polyvalent cation, for example $Ca^{2+}$, can be fed at a concentration of 0.05-50 mol of $Ca^{2+}$/mol of D-pantothenate, preferably 0.2-2 mol of $Ca^{2+}$/mol of D-pantothenate.

In step c) of the inventive process, the solution containing polyvalent salts of D-pantothenic acid is then worked up by nanofiltration, the polyvalent salts of D-pantothenic acid being enriched and simultaneously unwanted monovalent ions, preferably monovalent cations, for example ammonium, sodium or potassium ions, are depleted. In the inventive process, the content of monovalent cations, preferably ammonium, potassium and/or sodium ions, is reduced to a concentration of $\leq 5$ g/kg of solution.

The present invention comprises all commercially available nanofiltration systems. The separation is advantageously performed on asymmetrically structured porous membranes. In a preferred variant of the present process, membranes are used for this which are made up of a separation layer which carries out the actual separation, and a single- or multi-layered support layer which bears the separation layer and has coarser pores than the separation layer. The separation layers and the support layer can consist of organic polymers, ceramic, metal or carbon and must be stable in the reaction medium and at the process temperature. Preferred materials for the separation layer are polyamides, polyimides, or polypiperazines. The separation layers can also have a positive or negative surface charge. An example of an anionically functionalized nanofiltration membrane is the membrane DESAL 5 DK, but the present invention is not limited to the exclusive use of this membrane.

The membranes can be used in the form of flexible tubings, capillaries, hollow fibers or flat membranes, and in flat, tubular, multi-channel-element, capillary or coil modules which are known per se.

In advantageous variants of the inventive process, in the nanofiltration in step c), a pressure difference over the membrane in the range of 5-100 bar, preferably 20-80 bar, and particularly preferably 40-70 bar, is built up.

The process temperature is advantageously from 20 to 80° C., preferably from 30 to 60° C. In addition, the nanofiltration can be carried out in a manner known to those skilled in the art continuously or batchwise in one or more steps.

In a preferred variant, in each case before one or more nanofiltration step(s), a salt containing polyvalent cations is added in solid form or in aqueous solution.

According to the invention, the polyvalent cations are added as calcium and/or magnesium chloride, nitrate, hydroxide, formate, acetate, propionate, glycinate and/or lactate. In this case, as polyvalent cation, $Ca^{2+}$ can be fed at a concentration of 0.05-50 mol of $Ca^{2+}$/mol of D-pantothenate, preferably 0.2-2 mol of $Ca^{2+}$/mol of D-pantothenate (based on the state after mixing).

In the inventive process, salts containing polyvalent cations are added in solid form or aqueous solution during, preferably at the end of, or after, the fermentation in step a) or during or after the cell separation.

According to the invention, moreover, adding salts containing polyvalent cations during the nanofiltration step can be advantageous. In addition, an aqueous solution containing polyvalent cations can be supplied continuously.

In a further variant of the present process, it is conceivable that, in one or more process steps upstream of the nanofiltration solutions of differing product concentration can arise. Said solutions can be further processed by a nanofiltration in such a manner that said solutions are supplied in sequential nanofiltration steps in the order of ascending product concentrations.

According to the invention, as a result of the above-described inventive process, primarily the polyvalent salts of pantothenic acid are enriched in the retentate of the nanofiltration. In the permeate solution, principally the monovalent ions are enriched, when an anionically functionalized nanofiltration membrane is used, the monovalent cations are enriched. The content of monovalent cations, preferably ammonium, potassium and/or sodium ions, in the retentate can be reduced in this case to a concentration of $\leqq 5$ g/kg of solution. According to the invention the permeate of the nanofiltration or a part thereof can be recirculated to the fermentation in step a) of the inventive process. This recirculation of the permeate or parts thereof can be performed continuously. The above-described process steps carried out in addition to the nanofiltration serve for preconcentration or further concentration of D-pantothenate in the form of polyvalent salts.

A further advantage of the inventively used nanofiltration is that the reduction of the monovalent cations (in the retentate solution) can be accompanied simultaneously with a volume reduction of the retentate. The workup of the D-pantothenate-containing fermentation solution via nanofiltration can thus be used according to the invention as ion-exchange and concentration process for producing D-pantothenate.

This leads advantageously to a simplification, and simultaneously increased efficiency, of the subsequent process steps. For example, the energy consumption in drying can be significantly reduced on account of the concentration.

In a preferred embodiment of the present invention, the fermentation solution is freed from the cell mass by centrifugation and/or decantation and/or ultrafiltration. After adding from 0.05 to 50 mol ($Ca^{2+}$) ions/mol of pantothenate ion, preferably 0.2-2 mol $Ca^{2+}$ ions/mol of pantothenate ion, which are preferably charged in the form of a dilute solution having 0.01-10 mol of $Ca^{2+}/l$, the resultant solution is introduced into a nanofiltration module. The pressure difference across the membrane is in the range of about 5-100 bar, preferably about 20-80 bar, particularly preferably about 40-70 bar. Before or during the nanofiltration in this case, a $Ca^{2+}$-ion-containing aqueous solution can be added to the solution flowing across the membrane on the feed side. The retentate has a volume of 30-200% of the starting solution. In addition, about 5-99%, preferably 30-80%, of the monovalent cations present are removed.

The retentate preferably containing calcium D-pantothenate, magnesium D-pantothenate or a mixture thereof is then subjected to a drying and/or formulation. The drying and/or formulation of the calcium- and/or magnesium-D-pantothenate-containing solution is performed by methods known per se, for example spray drying, spray granulation, fluidized-bed drying, fluidized-bed granulation, drum drying, or spin-flash drying (Ullmann's Encyclopedia of Industrial Chemistry, 6th edition, 1999, electronic release, chapter "Drying of Solid Materials"). The gas inlet temperature in convection drying is in the range 100-280° C., preferably 120-210° C. The gas outlet temperature is 50-180° C., preferably 60-150° C. To establish a desired particle size distribution and the associated product properties, fine particles can be separated off and recirculated. In addition, coarse material can be ground in a mill and likewise then recirculated.

The inventive process has the advantages that unwanted cations are efficiently and virtually completely removed and at the same time a reduction in volume takes place which makes the subsequent process steps, in particular drying and/or formulation, simplified or more efficient. In addition, no product decomposition, or only extremely low product decomposition, takes place, with simultaneously high product yield. By feeding salt solutions of polyvalent cations during, or at the end of, fermentation, or during, or at the end of, an ultrafiltration or diafiltration, or during the nanofiltration step and/or by recirculating the permeate to the fermentation solution, the yields of D-pantothenate in the form of polyvalent, preferably divalent, ions, such as calcium or magnesium, are further increased.

In the above-described process, in addition, according to the invention reducing complex workup steps is advantageous, in particular omitting the use of organic solvents, with simultaneous provision of a desired product of good biological value. In addition, according to the invention the amount of wastewater produced is substantially reduced. This thus results in further savings in complex treatment and disposal plants. Thus the inventive process is advantageously distinguished in that it is simpler, less susceptible to faults, less time-consuming, significantly less expensive and thus more economical, than conventional processes.

However, this does not exclude the inventive process from being able to be varied. The previously described inventive process can be supplemented by one or more of the following process steps, each of which is familiar to those skilled in the art. In this case, all conceivable combinations of the following process steps with the process steps known to date are included according to the invention.

Thus the solutions resulting from the inventive process can be disinfected, for example by heating (sterilization) or other methods, for example pasteurization or sterile filtration.

In further variants of the inventive process, before drying and/or formulation of the retentate, at least one, or combinations, of the following steps can be carried out, comprising lysis and/or sterilization of the biomass and/or separation of the biomass from the fermentation solution and/or addition of further additives and/or concentration of the fermentation solution, preferably by removal of water.

The present invention thus also relates to a process in which the lysis and/or sterilization of the biomass is carried out while still in the fermentation solution, or not until after the biomass is separated off from the fermentation solution. This can be performed, for example, by a temperature treatment, preferably at 80-200° C., and/or an acid treatment, preferably with sulfuric acid or hydrochloric acid and/or enzymatically, preferably with lysozyme.

It is also conceivable for the cell mass present to be removed directly via the nanofiltration, that is to say simultaneously with the exchange of monovalent cations against polyvalent cations.

The solution resulting from the workup via nanofiltration can be concentrated before the drying and/or formulation via a suitable evaporator, e.g. falling-film evaporator, thin-film evaporator, or rotary evaporator. Such evaporators are manufactured, for example, by the company GIG (4800 Affnang Puchheim, Austria), GEA Canzler (52303 Düren, Germany), Diessel (31103 Hildesheim, Germany) and Pitton (35274 Kirchhain, Germany).

To improve the color properties of the end product, an additional filtration step can be carried out, in which a little activated carbon is added to the solutions obtained during the process and this suspension is then filtered. Or, the solutions obtained during fermentation can be passed through a small activated-carbon bed. The amounts of activated carbon used required for this are in the range of a few percent by weight of the solution and are within the knowledge and judgement of a person skilled in the art.

These filtrations can be simplified by adding a commercially conventional flocculant (e.g. Sedipur CF 902 or Sedipur CL 930 from BASF AG, Ludwigshafen) to the respective solution before filtration.

In an advantageous embodiment of the present invention, the fermentation output (fermentation broth) is sterilized by heating and then freed from the cell mass by centrifugation, filtration, ultrafiltration or decantation. After addition of 50-1 000 mg/kg, preferably 100-200 mg/kg, of a commercially conventional flocculant, based on the fermentation output, the suspension is filtered through a short bed of activated carbon and sand to obtained a biomass-free solution having a high D-pantothenic acid content. This treated solution is then treated by nanofiltration.

The subsequent drying of this solution can be performed, for example, by spray drying. This can be performed in cocurrent, countercurrent or mixed-stream flow. For atomization, all known atomizers can be used, in particular centrifugal atomizers (atomizer disk), single-fluid nozzle or two-fluid nozzle. Preferred drying temperature conditions are 150-250° C. tower inlet temperature and 70-130° C. tower outlet temperature. However, drying can also be performed at a higher or lower temperature level. To achieve very low residual moisture, a further drying step in a fluidized bed can be provided downstream.

The spray drying may also be carried out in an FSD or SBD dryer (FSD: fluidized spray dryer; SBD: spray bed dryer), as are constructed by the company Niro (Copenhagen, Denmark) and APV-Anhydro (Copenhagen, Denmark), which are a combination of spray-dryer and fluidized bed.

In spray drying, a flow aid can be added. As a result the deposits on the dryer wall can be reduced and the flow behavior particularly in the case of fine-grained powders, can be improved. Flow aids which can be used are, in particular, silicates, stearates, phosphates and corn starch.

In principle, drying can also take place in a spray fluidized bed, in which case this can be operated not only continuously but also batchwise. The solution can be sprayed in not only from the top (top-spray), from the bottom (bottom-spray), but also from the side (side-spray).

The present invention further relates to a composition for the use as animal feed additive and/or animal feed supplement, in which it can be prepared by
a) using at least one D-pantothenic-acid-producing organism, the pantothenic acid (pan) and/or isoleucine/valine (ilv) biosynthesis of which is deregulated and which forms at least 2 g/l of salts of D-pantothenic acid by fermentation in a culture medium, 0-20 g/l, preferably 0 g/l, of free β-alanine and/or β-alanine salt being fed to the culture medium,
b) feeding salts containing polyvalent cations to the D-pantothenate formed, polyvalent salts of D-pantothenic acid being produced,
c) treating the D-pantothenate-containing fermentation solution by nanofiltration, the polyvalent salts of D-pantothenic acid being enriched,
d) subjecting the nanofiltration retentate containing polyvalent salts of D-pantothenic acid to a drying and/or formulation.

In a variant of the present invention, a composition is comprised which can be prepared by, before the nanofiltration in step c), carrying out a removal of cell mass or components precipitated out in the solution, preferably by membrane filtration, particularly preferably by ultrafiltration, and very particularly preferably by diafiltration. The present invention further relates to a composition which can be prepared by feeding salts (in solid form or as aqueous solution) containing polyvalent cations during, or after, the removal of cell mass or components precipitated out in solution. According to the invention these salts, in a further variant, can also be supplied during the nanofiltration.

According to the invention the composition is further distinguished in that it contains salts of D-pantothenic acid in a concentration of at least 1-100% by weight, preferably 20-100% by weight and particularly preferably at least 50% by weight. The present invention relates to a composition which contains salts of D-pantothenic acid in the form of divalent cations, preferably calcium D-pantothenate and/or magnesium D-pantothenate. According to the invention preference is given to a composition which is distinguished in that the content of salts of D-pantothenic acid in the form of monovalent cations is $\leq 5$ g/kg.

According to the invention, owing to the above-described process, a calcium D-pantothenate or magnesium D-pantothenate is obtained which satisfies the requirements of a food additive. These requirements are, for example, a relatively high content of D-pantothenate, and a high compatibility for the target organism, and also a biological value in the sense of the "vitamin activity" of the inventive product.

The present invention is described in more detail by the examples below, which are not limiting for the invention, however:

EXAMPLE 1

In a laboratory fermenter equipped with agitator and gas-introduction device of 14 l capacity, aqueous fermentation medium of the following composition is charged:

| Starting material | Concentration [g/l] |
| --- | --- |
| Yeast extract | 5 |
| Soybean meal | 40 |
| Sodium glutamate · $H_2O$ | 5 |
| Ammonium sulfate | 8 |
| $KH_2PO_4$ | 5 |
| $K_2HPO_4$ | 10 |
| $NaH_2PO_4$ · 2 $H_2O$ | 6.15 |
| $NaH_2PO_4$ · 2 $H_2O$ | 12 |

After sterilization, the following sterile media components were added in addition:

| Starting material | Concentration [g/l] |
| --- | --- |
| Glucose · $H_2O$ | 20 |
| Calcium sulfate | 0.1 |
| Magnesium sulfate | 1 |
| Sodium citrate | 1 |
| $FeSO_4$ · 7 $H_2O$ | 0.01 |
| Trace salt solution | 1 ml |

The trace salt solution had the following composition: 0.15 g of $Na_2MoO_4.2H_2O$, 2.5 g of $H_3BO_3$, 0.7 g of $CoCl_2.6H_2O$, 0.25 g of $CuSO_4.5H_2O$, 1.6 g of $MnCl_2.4H_2O$, 0.3 g of $ZnSO_4.7H_2O$ were made up to 1 l with water. The trace salt solution was added through sterile filtration. The initial liquid volume was 5 l. The contents listed above are based on this value.

To this solution were added 100 ml of inoculation culture (OD=10) of *Bacillus subtilis* PA668 and the inoculated culture was fermented at 43° C. with vigorous stirring at a gas-flow rate of 12 l/min. This strain is described according to the annex of U.S. application serial No. 60/262,995.

In the course of 47 h, 2.1 l of a sterile aqueous solution were added. The composition was:

| Starting material | Concentration [g/l] |
|---|---|
| Glucose | 800 |
| Calcium chloride | 0.6 |
| Sodium glutamate · H$_2$O | 5 |
| Sodium citrate | 2 |
| FeSO$_4$ · 7 H$_2$O | 0.2 |
| Trace salt solution | 6 ml |

During the fermentation, the pH was kept at 7.2 by adding 25% strength ammonia solution or 20% strength phosphoric acid. Ammonia simultaneously acts as nitrogen source for the fermentation. The speed of rotation of the agitator element was controlled to keep the dissolved oxygen content at 30% of the saturation value. After terminating the addition of the carbon source, the fermentation was continued until the dissolved oxygen content (pO$_2$) had reached a value of 95% of the saturation value. The concentration of D-pantothenate at termination after 48 h was 22.8 g/l.

Similarly, fermentation broths can also be produced which give β-alanine-supply-free pantothenic acid titers greater than 20, 25, 30, 35, 40, 45, 50, 55, 60, 65, 70, 75, 80, 85, and >90 g/l.

EXAMPLE 2

7 000 ml of the fermentation output produced according to example 1 were subjected to ultracentrifugation, a ceramic monochannel tubular module (from Atech, Gladbeck, Germany) being used. In this case firstly a membrane having a pore width of 20 kD (10 nm) and secondly a membrane having a pore width of 50 nm were used.

The temperature in the experiments was 40° C., the overflow speed was 4 m/s and the transmembrane pressure (TMP= [p(feed)+p(retentate)]/2−p(permeate)), unless stated otherwise, was 1 bar.

Figure 1:
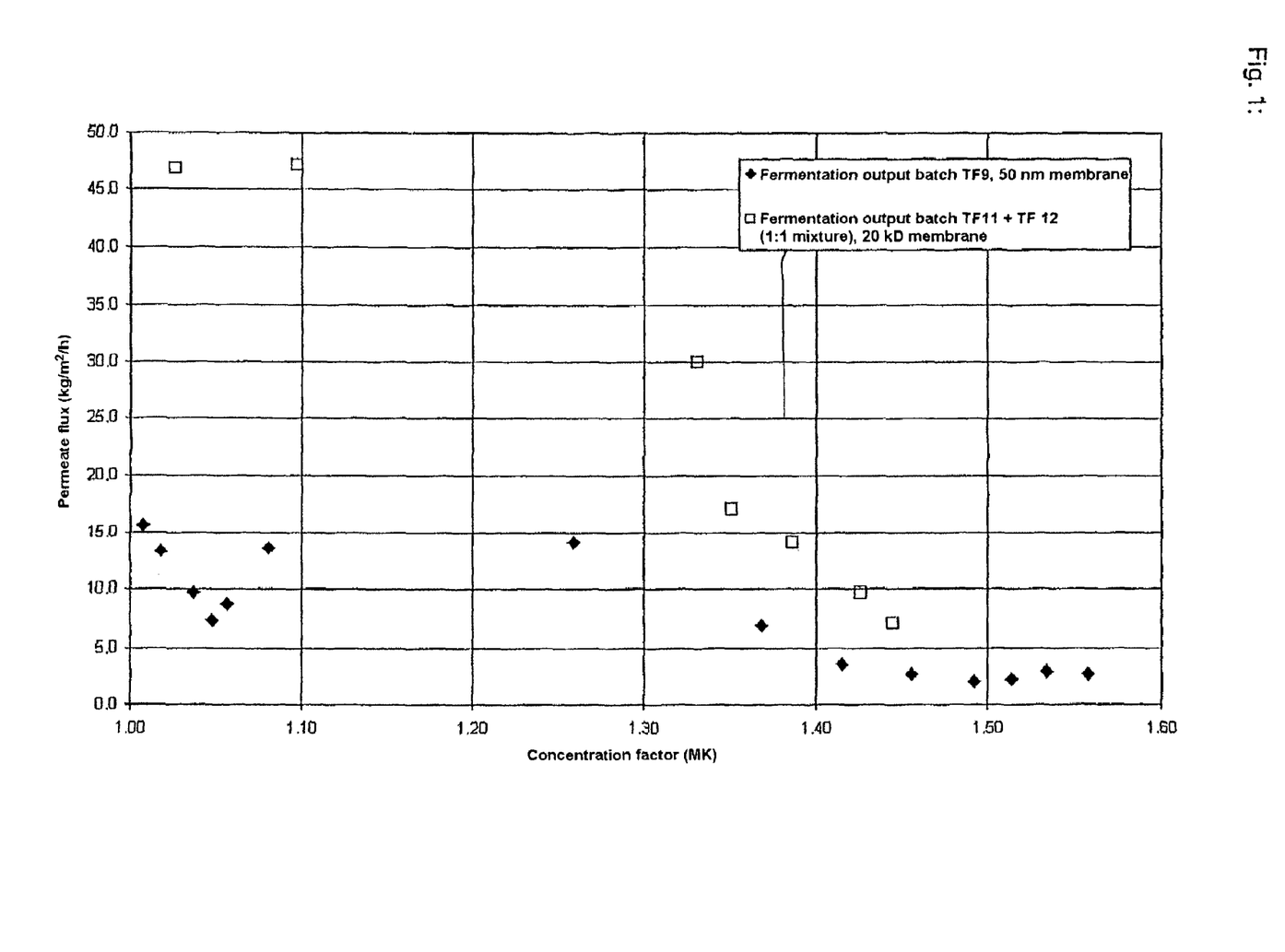
FIG. 1: Graphical presentation of transmembrane fluxes (permeate fluxes) of fermentation output during ultrafiltration as a function of concentration factor MK using membranes having a pore width of 50 nm and 20 kD.

In FIG. 1 the transmembrane fluxes (permeate fluxes) are plotted as a function of the concentration factor MK (MK(t) =$m_{feed}/m_{retentate}$ (t)).

It becomes apparent that the membrane having the lower pore width (20 kD) exhibits markedly higher fluxes than the membrane having the greater pore width (50 nm).

EXAMPLE 3

7 000 ml of the fermentation output, produced as under example 1, were subjected to ultrafiltration [sic] similar to example 2, the membrane used having a pore width of 20 kD.

Figure 2:
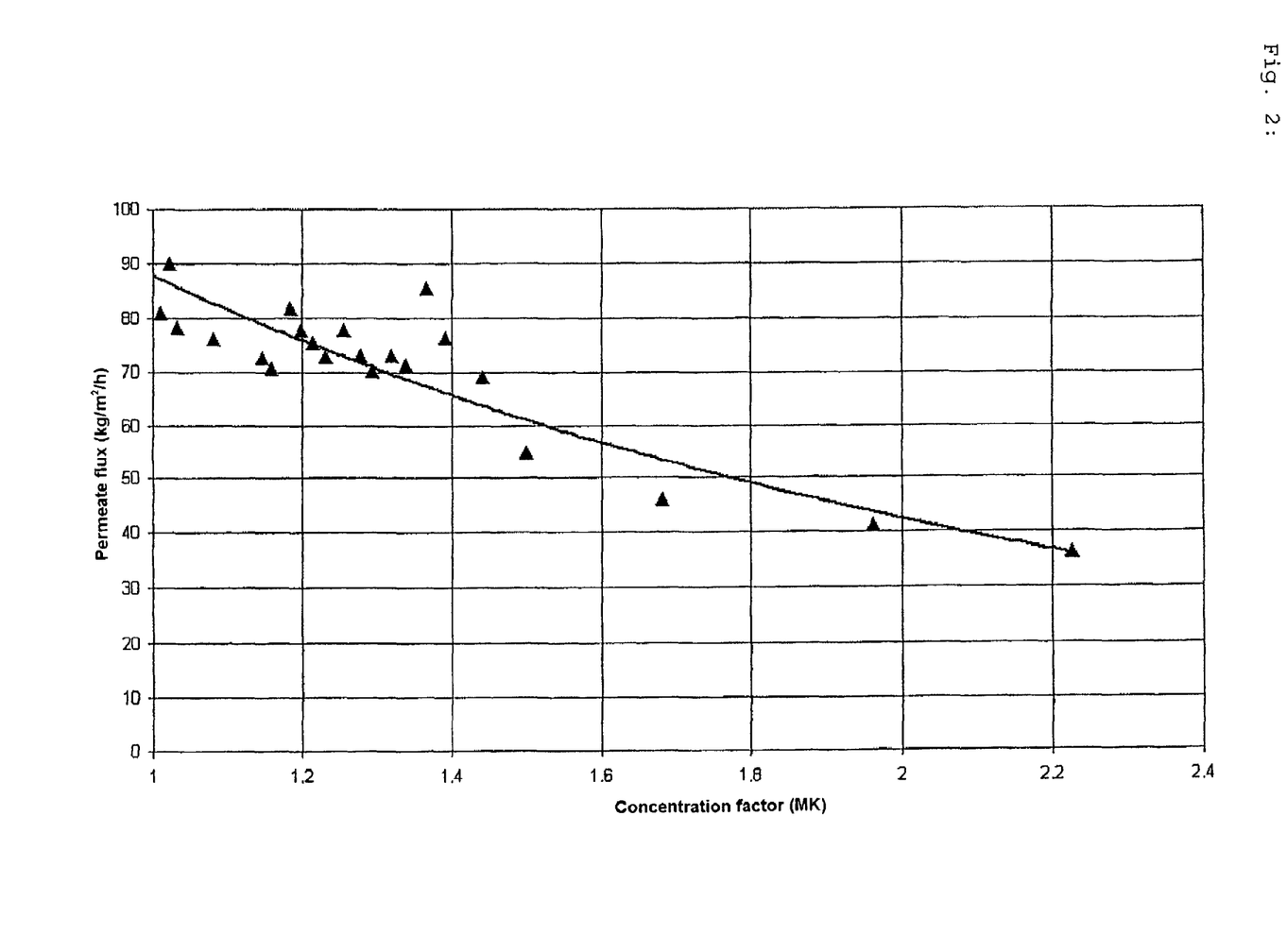
FIG. 2: Graphical presentation of transmembrane fluxes (permeate fluxes) of a centrifuged fermentation output during ultrafiltration as a function of concentration factor MK using a membrane having a pore width of 20 kD.

FIG. 2 shows that the concentration using fermentation output which had already been centrifuged is markedly higher than in example 2.

EXAMPLE 4

1 000 ml of an aqueous solution containing calcium pantothenate (according to table 3, column retentate feed) were placed in an agitator pressure cell having a maximum operating capacity of approximately 1.5 l. The "feed" pressure is generated in this cell by nitrogen overpressure and the membrane overflow was ensured by agitation using an anchor agitator driven by a magnetic coupling.

The nanofiltration membrane DESAL 5 DK, obtained from Osmonics Deutschland GmbH in Moers, was used.

Before, during and after the experiments with the abovementioned solution, to test the membrane integrity, rejection tests with MgSO$_4$ solution (2 000 ppm by weight) were carried out.

The rejection rate $R_i$ is listed in the two right-hand columns of table 3. Here the rejection rate is defined as follows: $R_i = 1 - c_{i,permeate}/c_{i,retentate}$; where $R_i$=rejection rate for component i, $c_{i,permeate}$=concentration of component i in the permeate, $c_{i,retentate}$=concentration of component i in the retentate.

The concentrations mean the concentrations instantaneously established in the non-steady state experiment at a defined timepoint, but not the concentration in the fractions resulting after the end of the experiment. The rejection rate $R_i$, in the ideal case, is concentration-independent, which was also used as a basis in calculating the reported values from the concentrations in the fractions.

From table 3 it follows that Ca$^{2+}$ and pantothenate have rejection rates of 84% and 99%, respectively, that is to say are present in the retentate.

EXAMPLE 5

In the workup of an aqueous solution of Na pantothenate (0.2 mol/l), under similar conditions to example 4, a concentration by nanofiltration was carried out. Table 4 shows that the rejection rate of pantothenate is 80%.

EXAMPLE 6

Concentrating an equimolar solution of NaCl/CaCl$_2$ under similar conditions to example 4 is summarized in table 5. Here it can be seen that the rejection rate of the membrane for Ca$^{2+}$ of 41% or 42% is relatively low compared with the high rejection rate of calcium in combination with pantothenate (example 5).

Legend to the Figures and Tables

Table 1: Outline of asymmetrically structured membranes for separating off cell mass or components precipitated out in solution.

Table 2: Outline of membranes and their properties for separating off cell mass or components precipitated out in solution.

Table 3: Outline of the analytical values of nanofiltration, especially with respect to the rejection rate of calcium ions and pantothenate, in an aqueous solution containing 0.1 mol/kg of Ca pantothenate and 0.2 mol/kg of NaCl.

Table 4: Outline of the analytical values of nanofiltration, especially with respect to the rejection rate of calcium ions and pantothenate, in an aqueous solution containing 0.2 mol/l of Na pantothenate and 0.1 mol/l of CaCl$_2$.

Table 5: Outline of the analytical values of nanofiltration, especially with respect to the rejection rate of calcium ions, in an aqueous solution containing equimolar amounts of NaCl and $CaCl_2$.

We claim:

1. A process for preparing D-pantothenic acid and/or salts thereof, which comprises
    a) fermenting at least one D-pantothenic-acid-producing bacterium from the Bacillaceae family, the pantothenic acid (pan) and optionally the isoleucine/valine (ilv) biosynthesis of which is deregulated and which forms at least 2 g/l of salts of D-pantothenic acid by fermentation in a culture medium,
    b) salts containing polyvalent cations being fed to the D-pantothenate formed, polyvalent salts of D-pantothenic acid being formed,
    c) the solution containing polyvalent salts of D-pantothenic acid being worked up by nanofiltration, the polyvalent salts of D-pantothenic acid being enriched and
    d) the nanofiltration retentate containing polyvalent salts of D-pantothenic acid being subjected to drying and/or formulation, wherein free β-alanine and/or β-alanine salt is not fed to the culture medium, and wherein deregulated panthothenic acid biosynthesis is achieved by overexpressing one or more genes in the pan and optionally in the ilv synthesis pathways, wherein said overexpressed genes include at least the panD gene.

2. A process as claimed in claim 1, wherein the bacterium is of the genus *Bacillus*.

3. A process as claimed in claim 1, wherein, in step a), a content of D-pantothenic acid and/or salts thereof of at least 10 g/l of culture medium is formed.

4. A process as claimed in claim 1, wherein cell mass or components precipitated out in the solution is/are separated off before the nanofiltration in step c).

5. A process as claimed in claim 4, wherein the separation is carried out by decanting or membrane filtration.

6. A process as claimed in claim 5, wherein the membrane filtration is carried out as diafiltration.

7. A process as claimed in claim 5, wherein salts containing polyvalent cations are added in solid form or aqueous solution during, at the end of, or after, the fermentation in step a) or during, or after, a membrane filtration of a D-pantothenate-containing solution.

8. A process as claimed in claim 7, wherein salts containing polyvalent cations are added in solid form or aqueous solution during a nanofiltration.

9. A process as claimed in claim 7, wherein an aqueous solution containing polyvalent cations is fed continuously.

10. A process as claimed in claim 7, wherein the polyvalent cations are added as calcium and/or magnesium chloride, nitrate, hydroxide, formate, acetate, propionate, glycinate and/or lactate.

11. A process as claimed in claim 7, wherein the polyvalent cation fed is $Ca^{2+}$ at a concentration of 0.05-50 mol of $Ca^{2+}$/mol of D-pantothenate.

12. A process as claimed in claim 1, wherein, in the nanofiltration in step c), a pressure difference across the membrane in the range of 5-100 bar is built up.

13. A process as claimed in claim 1, wherein the nanofiltration in step c) reduces the content of monovalent cations to a concentration of $\leq 5$ g/kg of solution.

14. A process as claimed in claim 1, wherein the permeate from step c) or a part thereof is recirculated to the fermentation in step a).

15. A process as claimed in claim 1, wherein the permeate or parts thereof are recirculated continuously.

16. A process as claimed in claim 1, wherein the retentate from c) is a suspension containing polyvalent salts of D-pantothenic acid.

* * * * *